(12) United States Patent
Ghahi et al.

(10) Patent No.: US 12,343,034 B2
(45) Date of Patent: Jul. 1, 2025

(54) CATHETER FOR ASPIRATION, FRAGMENTATION AND REMOVAL OF REMOVABLE MATERIAL FROM HOLLOW BODIES

(71) Applicant: STRAUB MEDICAL AG, Wangs (CH)

(72) Inventors: Saeid Kasiri Ghahi, Vilters (CH); Mohsen Zendehbad, Pfaffhausen (CH); Abdallah Regaig, Bad Ragaz (CH); Bruno Bahnmueller, Zurich (CH)

(73) Assignee: Straub Medical AG, Wangs (CH)

( * ) Notice: Subject to any disclaimer, the term of this patent is extended or adjusted under 35 U.S.C. 154(b) by 698 days.

(21) Appl. No.: 17/772,845

(22) PCT Filed: Oct. 26, 2020

(86) PCT No.: PCT/EP2020/080022
§ 371 (c)(1),
(2) Date: Apr. 28, 2022

(87) PCT Pub. No.: WO2021/083832
PCT Pub. Date: May 6, 2021

(65) Prior Publication Data
US 2023/0000514 A1 Jan. 5, 2023

(30) Foreign Application Priority Data
Oct. 30, 2019 (EP) ..................... 19206321

(51) Int. Cl.
*A61B 17/22* (2006.01)
*A61B 17/3207* (2006.01)

(52) U.S. Cl.
CPC ............... *A61B 17/3207* (2013.01); *A61B 2017/22079* (2013.01); *A61B 2217/005* (2013.01)

(58) Field of Classification Search
CPC ............... A61B 17/3207; A61B 17/22; A61B 2017/22079; A61B 2217/005; A61B 2017/00685; A61B 17/320758
See application file for complete search history.

(56) References Cited

U.S. PATENT DOCUMENTS

| 5,226,909 A | 7/1993 | Evans et al. |
| 5,873,882 A | 2/1999 | Straub et al. |

(Continued)

FOREIGN PATENT DOCUMENTS

| CN | 101123918 A | 2/2008 |
| CN | 101511284 A | 11/2011 |

(Continued)

OTHER PUBLICATIONS

Chinese Office Action and translation for Appln. No. 202080076366.0, mailed Jul. 9, 2024, 18 pages.

(Continued)

*Primary Examiner* — David Hamaoui
*Assistant Examiner* — Adreanne A. Arnold
(74) *Attorney, Agent, or Firm* — Dinsmore & Shohl LLP

(57) ABSTRACT

The invention refers to a catheter (51) for aspiration, fragmentation and removal of removable material from blood vessels. The catheter (51) comprises a flexible tube (52), a flexible helical transport screw (62) inside of the flexible tube (52), a stopper element (82) for providing an abutment for the distal end (64) of the flexible helical transport screw (62). The stopper element (82) is provided spaced from the distal end of the catheter (51), thereby defining a distal region (56) of the catheter (51) extending from the stopper element (82) in direction to the distal end of the catheter (51) which is free of rotational elements inside. A suction open- (Continued)

Figure 1:
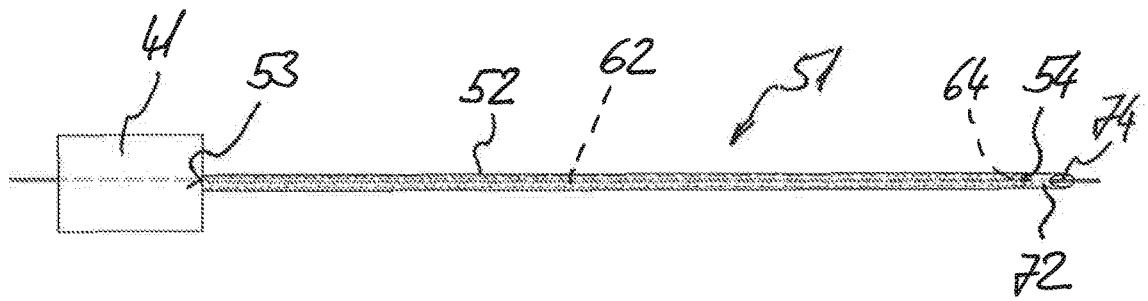

ing (74) for aspiration of the removable material into the inside of the flexible tube (52) is provided in the distal region (56) of the catheter (51).

14 Claims, 5 Drawing Sheets

(56) References Cited

U.S. PATENT DOCUMENTS

| | | | |
|---|---|---|---|
| 6,238,405 | B1 | 5/2001 | Findlay, III et al. |
| 8,568,432 | B2 | 10/2013 | Straub |
| 2006/0206127 | A1 | 9/2006 | Conquergood et al. |
| 2006/0206133 | A1 | 9/2006 | Conquergood et al. |
| 2008/0004643 | A1 | 1/2008 | To et al. |
| 2010/0125253 | A1 | 5/2010 | Olson et al. |
| 2011/0313346 | A1 | 12/2011 | Straub |
| 2016/0331645 | A1 | 11/2016 | Bagwell et al. |
| 2018/0296233 | A1 | 10/2018 | Schwager |
| 2019/0038300 | A1* | 2/2019 | Savastano ............ A61M 25/09 |

FOREIGN PATENT DOCUMENTS

| | | | |
|---|---|---|---|
| CN | 102481158 | A | 5/2012 |
| EP | 1176915 | A1 | 2/2002 |
| JP | 2010532211 | A | 10/2010 |
| JP | 2012509733 | A | 4/2012 |
| JP | 2014501552 | A | 1/2014 |
| WO | 0051504 | A1 | 9/2000 |
| WO | WO-2009005779 | A1 * | 1/2009 ............ A61B 17/22 |
| WO | 2012058438 | A1 | 5/2012 |

OTHER PUBLICATIONS

International Preliminary Report on Patentability—Form PCTIPEA416 mailed Jun. 21, 2021, in International Application No. PCT/EP2020/080022.

Japanese Office Action dated Mar. 12, 2024 pertaining to Japanese application No. 2022-52576 filed Apr. 28, 2022, pp. 1-4.

Chinese Office Action for Appln. No. 202080076366.0, mailed Jan. 27, 2025, 19 pages (with English Translation).

* cited by examiner

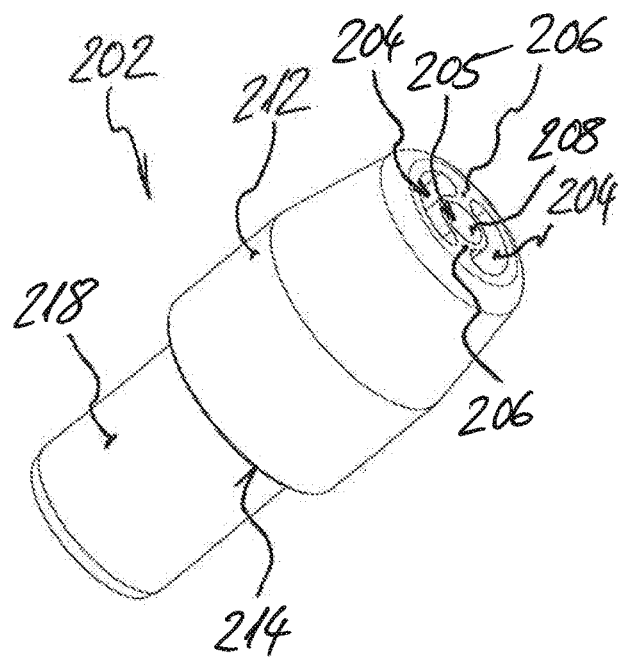
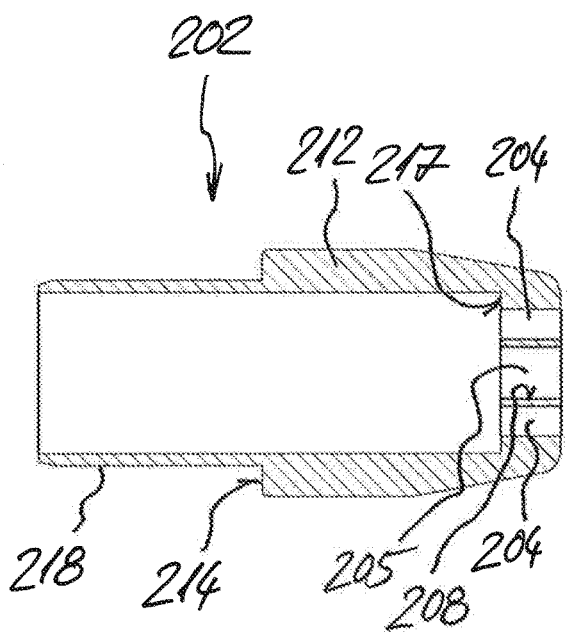
FIG 21  FIG 22
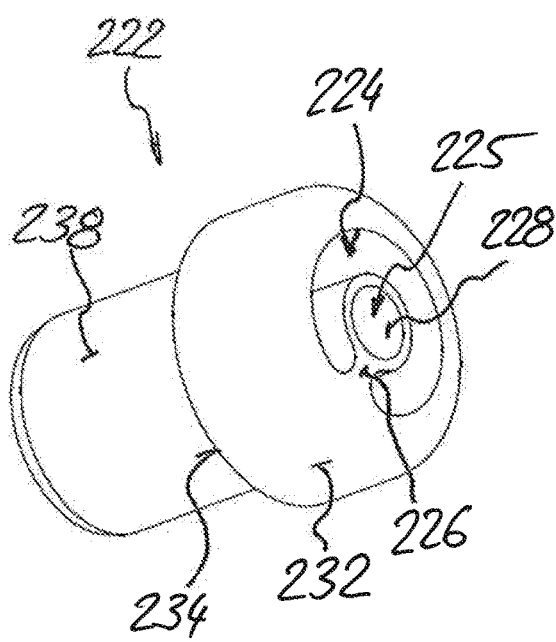
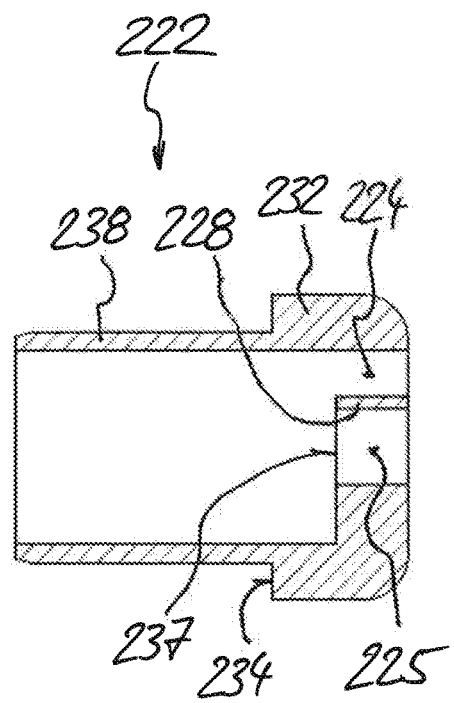
FIG 23  FIG 24

CATHETER FOR ASPIRATION, FRAGMENTATION AND REMOVAL OF REMOVABLE MATERIAL FROM HOLLOW BODIES

CROSS-REFERENCE TO RELATED APPLICATIONS

This application is a National Stage Entry, under 35 U.S.C. § 371, of International Patent Application No. PCT/EP2020/080022, filed Oct. 26, 2020, which claims priority to EP Application Serial No. 19206321.2, filed Oct. 30, 2019, the contents of which are hereby incorporated by reference in their entirety.

The invention refers to a catheter for aspiration, fragmentation and removal of removable material, in particular thrombi and emboli, from hollow bodies, in particular blood vessels, according to claim 1.

Such catheters are used in particular for the treatment of occlusive vascular diseases by aspiration, fragmentation and removal of emboli and thrombi. They are introduced into the artery or vein and advanced, preferably with X-ray monitoring, up to the narrowed or blocked area that is to be treated. A fragmentation tool drivable in a rotary manner by means of a rotary drive is arranged at the distal (front) end of the catheter.

In the case of these catheters, a distinction should be made as a rule on the basis of two different fields of use:
A) Atherectomy: This is the removal of, as a rule, hard deposits that have adhered to the vessel walls over many years.
B) Thrombectomy: This is the removal of blood clots that accumulate at bottlenecks and lead to blockage of the blood vessels (emboli).

A rotational catheter disclosed, for example, in EP 0 267 539 B1 and intended for atherectomy has, as a cutting tool, a substantially ellipsoidal cutter whose surface is provided with abrasive material and that is driven via a flexible drive shaft by a rotary drive arranged at the proximal end of the catheter at a speed of up to 160,000 rpm. The cutter is connected to the flexible drive shaft. The drive shaft runs in a tubular sheath serving as a catheter tube. A guide wire, which is introduced into a blood vessel before the introduction of the catheter, is advanced to the area to be treated or slightly beyond, and serves as a guide for the cutter and the drive shaft, extends through the drive shaft.

In the case of these known rotational catheters, the risk that the vessel wall will be injured and in certain circumstances even perforated, particularly in pronounced curves of the blood vessel, cannot be ruled out.

U.S. Pat. No. 5,226,909 A discloses another atherectomy catheter that has, on its working head, a sleeve-like or helical cutting element drivable by a rotary drive and/or displaceable in the axial direction. The opening of the working head is pressed against the deposits adhering to the vessel wall by means of a lateral inflatable balloon. These deposits are then comminuted by rotation or axial advance of the cutting element and are collected in a chamber.

Disadvantageously of this known solution is that the chamber must then be emptied from time to time by withdrawing the catheter. Continuous removal of comminuted deposited material is not envisaged.

U.S. Pat. No. 5,873,882 A describes a rotational catheter for atherectomy, whose working head includes a stationary stator, connected to a tube, and a rotor. The rotor is rotatable relative to the stator by means of a high-speed transport/drive screw. Both the stator and the rotor have, at their circumference, windows that can be caused to coincide. As a result of shearing between a cutting edge on the rotor and an opposite cutting edge on the openings of the stator, comminution of the parts projecting into or sucked into the openings is effected. The rotor may surround the stator on the outside ("outer rotor") or may be arranged in the interior of the stator ("inner rotor").

Catheters having inner and outer rotors with cutting edges that operate around the catheter axis may stir up blood and occlusion material, so that the blood flow from proximal to distal may wash away particles that may again produce blockages and blood flow problems in other areas of the blood circulation, particularly in small blood vessels.

US 2006/0206133 A1 shows a removal device for removal of tumor tissue from a patient's body. The removal device comprises an elongated member having a proximal end and a distal end, a tissue removal member extending from the proximal end of the elongated member inside of the elongated member in direction of the distal end of the elongated member. The tissue removal member has a distal end spaced from the distal end of the elongated member, thereby defining a distal region of removal device extending from distal end of the tissue removal member in direction to the distal end of the elongated member which is free of rotational elements inside. The tissue removal member is provided with helically extending transport surfaces and is rotatable by a drive means. Suction openings for aspiration are provided in the distal region of the removal device.

Disadvantageously of this known solution is that the stiff elongated member and the stiff removal member cannot be used as catheter in artery or vein due their stiffness.

Therefore, the object of the present invention is to overcome at least some of the disadvantages of the before described solution and to provide a catheter, in particular for atherectomy, that operates in an atraumatic manner and can aspirate and fragment thrombi and emboli in the blood vessel and transport them through the catheter tube continuously out of the vessel, whereby the risk of injury to walls of blood vessels is minimized. The advantages of known systems, in particular those of the system according to U.S. Pat. No. 5,873,882 A are however to be retained.

This object is solved by the features of the independent claim. Advantageous developments are set out in the figures, in the description and in the dependent claims.

According to the invention a catheter for aspiration, fragmentation and removal of removable material, in particular thrombi and emboli, from hollow bodies, in particular blood vessels, comprising:
  a flexible tube, the flexible tube having a proximal end and a distal end,
  a flexible helical transport screw, the flexible helical transport screw extending from the proximal end of the flexible tube inside of the flexible tube in direction of the distal end of the flexible tube and the flexible helical transport screw having a distal end, wherein said flexible helical transport screw is provided with helically extending transport surfaces and is rotatable by a drive means,
  a stopper element for providing an abutment for the distal end of the flexible helical transport screw, wherein the stopper element is provided spaced apart from the distal end of the catheter, thereby defining a distal region of the catheter extending from the stopper element in direction to the distal end of the catheter, which is free of rotational elements inside,
  at least one suction opening for aspiration of said removable material into the inside of the flexible tube, wherein the at least one suction opening is provided in the distal region of the catheter.

By such a catheter no shearing, cutting or rotating elements are exposed to the vessel wall during any treatment stages. The stopper element prevents the flexible helical transport screw from entering into the at least one suction opening during the use and, thereby preventing the flexible helical transport screw from being exposed to the vessel wall. Especially, during introduction of the catheter and/or during the use inside the vessels or vein the distal end of the flexible helical transport screw cannot protrude from the flexible tube. The flexible helical transport screw is a flexible element and can also be stretched longitudinally. Axial force and stretching can occur as an example as a result of a blockage or kinking in the flexible tube. This may result in the extension of the flexible helical transport screw (screwing out) in direction of the distal end of the flexible tube. Also in this case, the stopper prevents the flexible helical transport screw from entering into the at least one suction opening during the use.

The stopper element also prevents the vessel wall from getting in contact with the flexible helical transport screw. The rotation of the flexible helical transport screw generates a negative pressure and provides a continuous aspiration and transportation of material outside the patient body.

The catheter comprises at least one or more suction openings for aspiration. The number and the size of the of suction openings can be related to the safety and performance of the catheter.

The flexible helical transport screw may have an inner support element such as a wire or tube. The inner support element may be attached to the flexible helical transport screw.

The stopper element may be connected directly or by another means such as a connecting tube to the flexible tube. The connecting tube can be flexible for the intended use. The connecting tube is preferably designed or made from a material to be kink-resistant or is supported internally in a way that will not kink during the use.

Preferably the stopper element having a distal end and a proximal end and the stopper element having a sleeve-like shape with a first inner diameter and a front opening having at least one circumferential surface and at least partly at least one abutment surface for abutment for the distal end of the flexible helical transport screw. Thereby, between distal end of the flexible helical transport screw and the at least one abutment surface of the stopper element a shearing effect is created in order to cut the material ready for transport. By this shearing effect the size of the particles is further reduced and the transport of the fragmented material is facilitated. The removable material will be crushed in particles when entering the at least one suction opening. However, by this shearing effect the size of the particles is further reduced and the transport is facilitated.

As a further preferred alternative, the stopper element having a distal end and a proximal end and the stopper element having a sleeve-like shape with a first inner diameter and a front opening having at least a second inner diameter and at least one circumferential surface, whereby the at least second inner diameter is smaller than the first inner diameter. The removed material will enter the catheter through the front opening whereby—as per venturi effects— causes an additional strain to the aspirated material and thus contributes to fragmenting the aspirated material which is then removed by the flexible helical transport screw outside the body. In other words, axial change of the lumen area, which originates from the difference between the lumen area of the stopper in comparison to the lumen area of the distal region of the catheter and/or to the lumen area of the flexible tube. This axial change creates a pressure gradient which, from fluid dynamics point of view, results in an additional strain on the occluding material and helps for the cutting process.

Preferably the at least one circumferential surface of the front opening of the stopper element is conically shaped, in particular narrowing in the direction of the proximal end of the stopper element, whereby the venturi effects are enhanced.

Preferred the stopper element comprising an additional abutment element for providing an abutment for the distal end of the flexible helical transport screw, whereby the shearing effect at the distal end of the flexible helical transport screw may be improved. Additionally or alternatively, by the additional abutment element a friction may be reduced at the distal end of the flexible helical transport screw which result in lower temperature levels at this region and a longer usability of the catheter. Furthermore, the rotation speed for rotating of the flexible helical transport screw may be increased what secures a faster transportation of the fragmented material and therefore reduces the duration of the procedure.

In particular the additional abutment element is provided inside of the stopper element, whereby the aforementioned effects can be realized in an easy constructive way.

Preferred the stopper element comprises at least partly from radiopaque material, whereby the user can easily use the catheter during surgical procedure. The stopper element can be made from different materials or a combination of different materials. Also, the material might change along the stopper element to make it atraumatic. Some examples of the materials for the stopper element are metals, such as stainless steel, or polymers, for example as a non-exhaustive list: Polyamide, Pebax® and Polyetheretherketon (PEEK). Should for any specific reason the selected material not be radiopaque, it will be either mixed with a radiopaque material or will feature a radiopaque marker.

Preferably a catheter end piece is provided defining at least partly the distal region of the catheter, wherein the catheter end piece comprising the at least one suction opening and wherein catheter end piece is connected to the distal end of the flexible tube. This catheter end piece, may be called head piece or head of the catheter, can be formed according to the required functional needs. E.g., the catheter end piece is a section of the flexible tube whereby the at least one suction opening is provided at this section. Alternatively, the catheter end piece is a separate piece, optionally made from a material different from the material of the flexible tube. The material of such a catheter end piece is chosen according the respective requirements.

Preferred the catheter end piece comprising at least two suction openings, thereby secure a removal of material also if one of the suction openings is blocked be aspirated material.

In particular the at least two suction openings are arranged opposite of each other, whereby a good removal is secured. By this embodiment a removal takes also place, if the catheter end piece is placed inside emboli during the use of the catheter.

Preferably the catheter end piece comprising at least one suction opening at the distal end of the catheter end piece, thereby secure a removal of material also from the distal end.

Preferred the stopper element is an abutment surface provided inside of the catheter end piece, whereby an easy constructive embodiment can be realized.

Preferably the catheter end piece comprising a guide wire opening for pass through the guide wire through the catheter end piece, whereby a correct guidance of the catheter inside of the hollow body is secured.

Preferred the guide wire opening of the catheter end piece is arranged at least partly inside of the at least one suction opening, whereby a correct guidance of the catheter inside of the hollow body is secured.

Preferably the catheter end piece comprising a connection section for connecting the catheter end piece to the flexible tube, whereby an easy connection between a separate catheter end piece and the flexible tube can be realized.

The catheter end piece may be connected directly or by another means such as a connecting tube to the flexible tube. The connecting tube can be flexible for the intended use. The connecting tube is preferably designed or made from a material to be kink-resistant or is supported internally in a way that will not kink during the use.

Instead of a fixation of the stopper element to the flexible tube, the stopper element may be connected directly or by another means to the catheter end piece.

Preferred the catheter end piece comprises at least partly from radiopaque material, whereby the user can easily use the catheter during surgical procedure. The catheter end piece can be made from different materials or a combination of different materials. Also, the material might change along the catheter end piece to make it atraumatic. Some examples of the materials for the catheter end piece are metals, such as stainless steel, or polymers, for example as a non-exhaustive list: Polyamide, Pebax® and Polyetheretherketon (PEEK). Should for any specific reason the selected material not be radiopaque, it will be either mixed with a radiopaque material or will feature a radiopaque marker band.

Further advantages, features and details of the invention result from the following description, in which execution examples of the invention are described with reference to the drawings.

The list of reference signs and the technical content of the patent claims and figures are part of the disclosure. The figures are described coherently and comprehensively. Same reference signs mean same components, reference signs with different indices indicate functionally identical or similar components.

Figure 2:
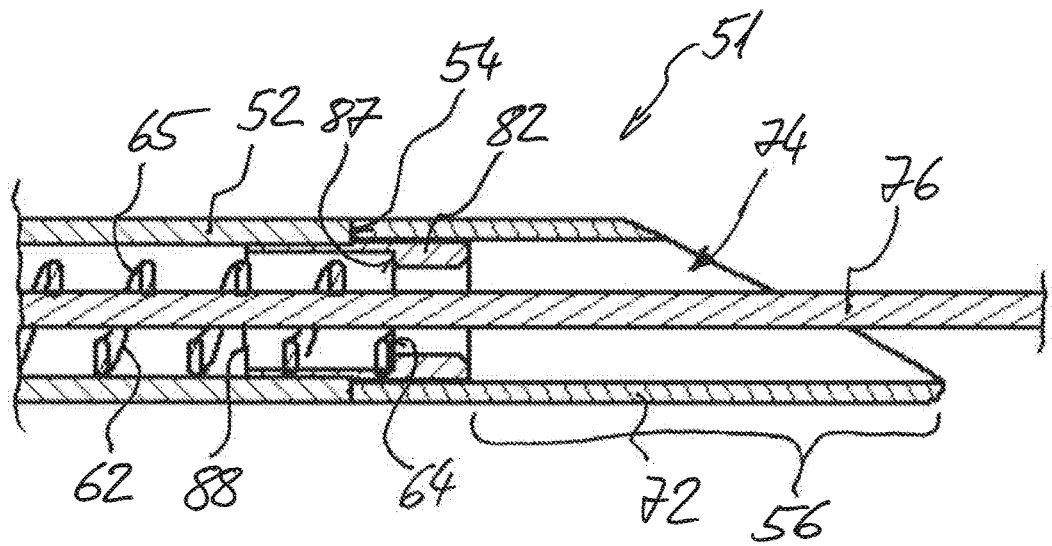
Figures 3, 4:
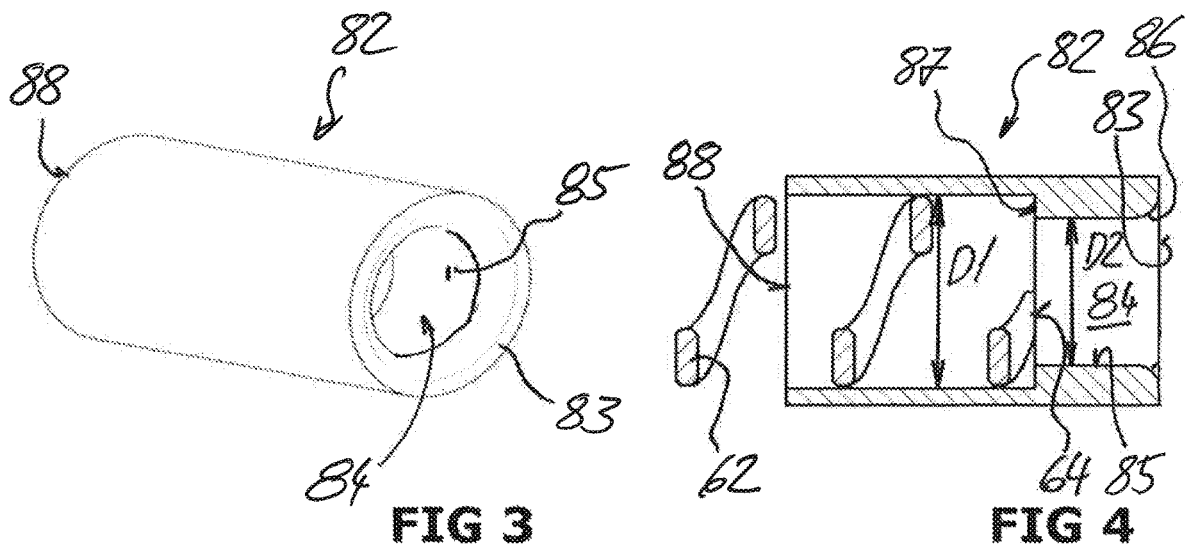
Figure 5:
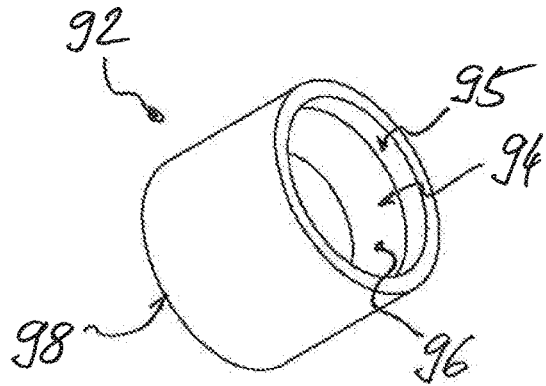
Figure 6:
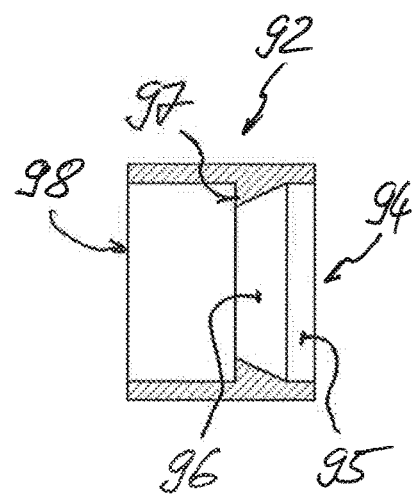
Figure 7:
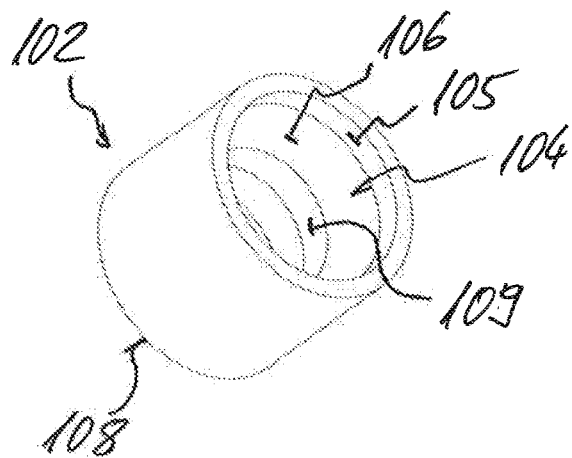
Figure 8:
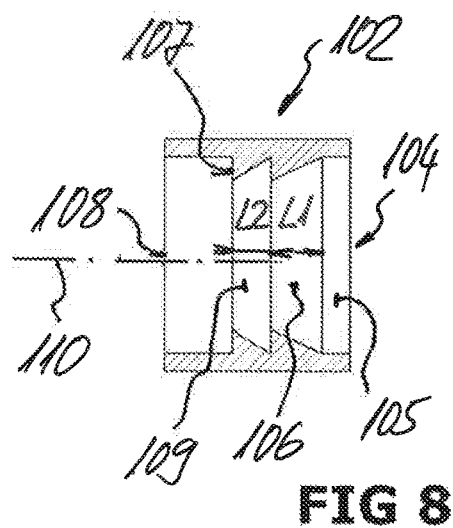
Figure 9:
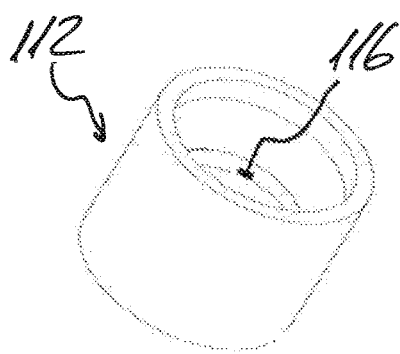
Figure 10:
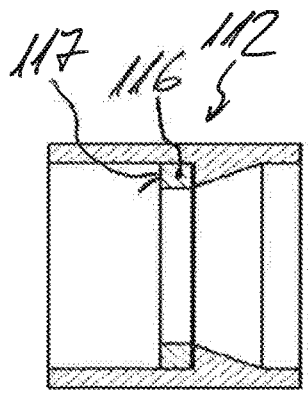
Figure 11:
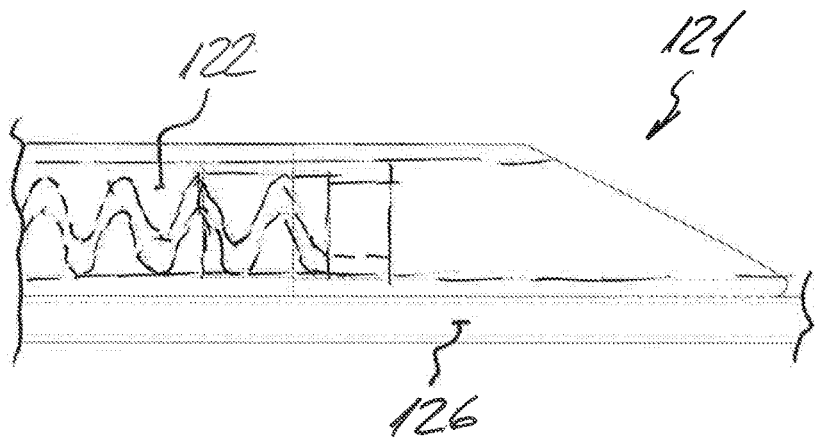
Figure 12:
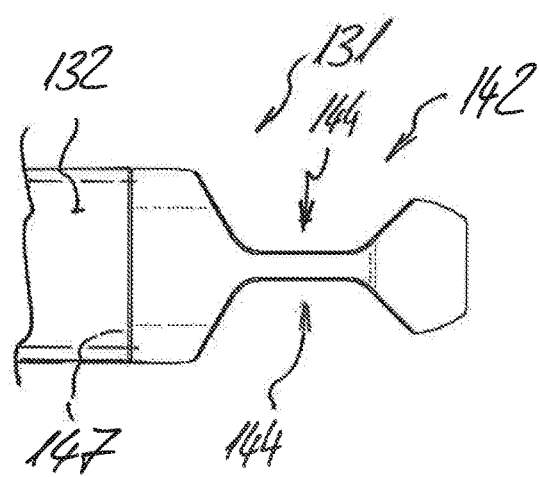
Figure 13:
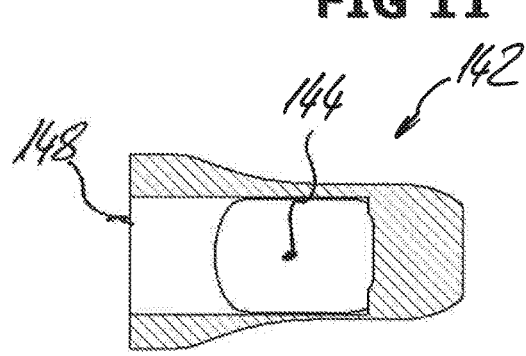
Figure 14:
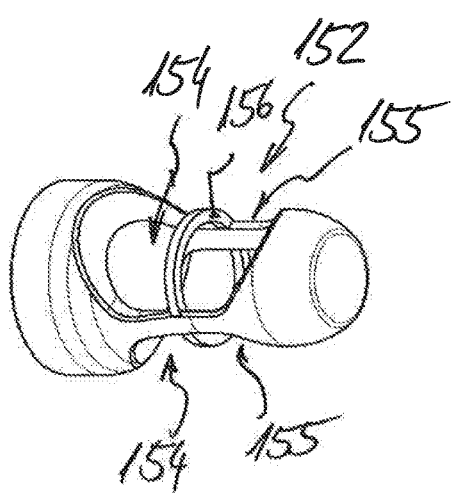
Figure 15:
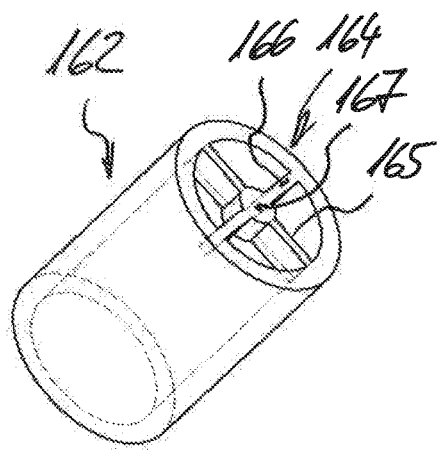
Figure 16:
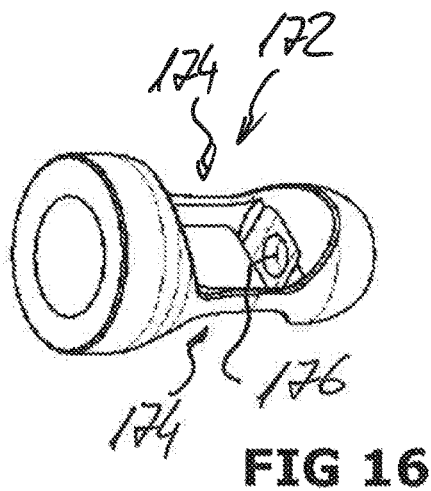
Figure 17:
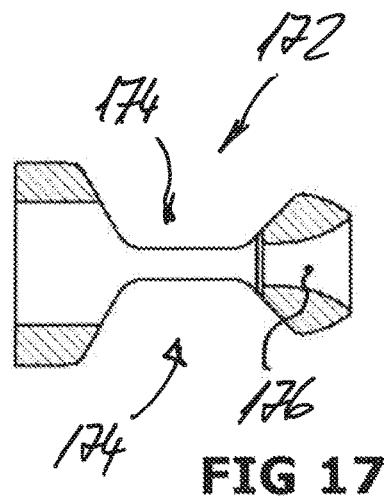
Figure 18:
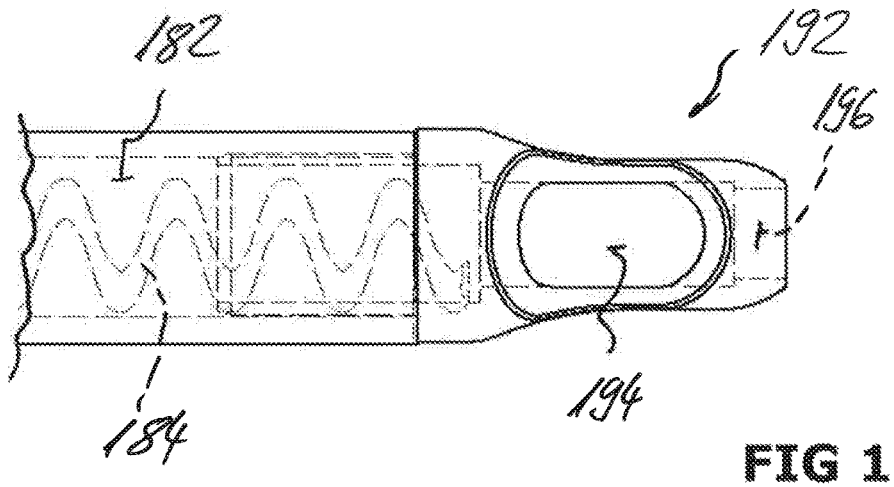
Figure 19:
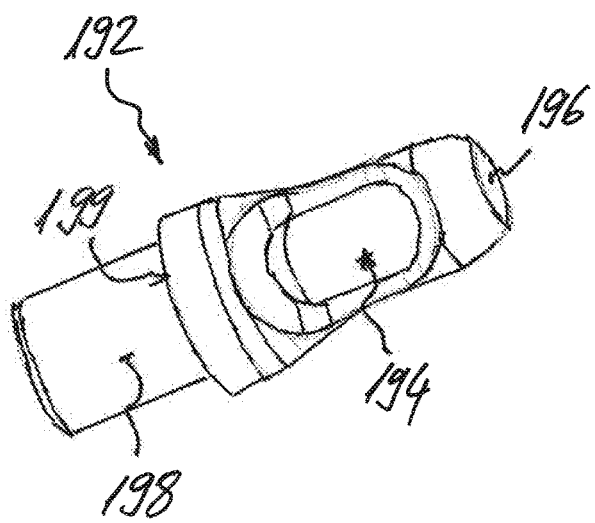
Figure 20:
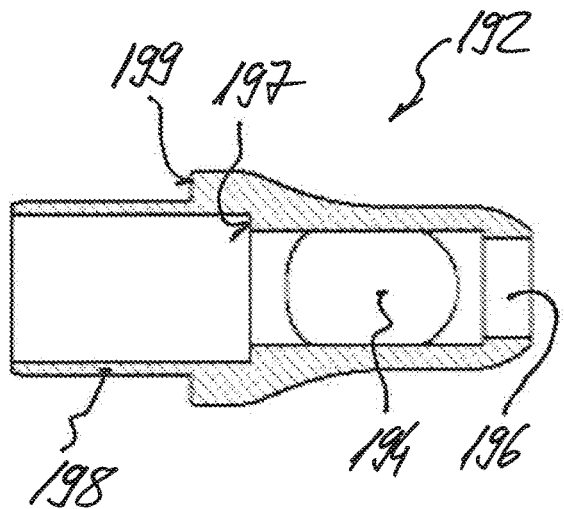

Showing it:

FIG. 1 a first embodiment of an inventive catheter in a side view,

FIG. 2 a partial sectional view of the distal end of the catheter according to FIG. 1, FIG. 3 a first embodiment of a stopper element in a perspective view, FIG. 4 a sectional view of the stopper element according to FIG. 3, FIG. 5 a second embodiment of a stopper element in a perspective view, FIG. 6 a sectional view of the stopper element according to FIG. 5, FIG. 7 a third embodiment of a stopper element in a perspective view, FIG. 8 a sectional view of the stopper element according to FIG. 7, FIG. 9 a fourth embodiment of a stopper element in a perspective view, FIG. 10 a sectional view of the stopper element according to FIG. 9, FIG. 11 a partial side view of the distal end of a catheter, FIG. 12 a first embodiment of a catheter end piece element in a perspective view, FIG. 13 a sectional view of the catheter end piece element according to FIG. 12, FIG. 14 a second embodiment of a catheter end piece element in a perspective view, FIG. 15 a fifth embodiment of a stopper element in a perspective view, FIG. 16 a third embodiment of a catheter end piece element in a perspective view, FIG. 17 a sectional view of the catheter end piece element according to FIG. 16, FIG. 18 a partial side view of the distal end of a catheter, FIG. 19 a fourth embodiment of a catheter end piece element in a perspective view, FIG. 20 a sectional view of the catheter end piece element according to FIG. 19, FIG. 21 a fifth embodiment of a catheter end piece element in a perspective view, FIG. 22 a sectional view of the catheter end piece element according to FIG. 21, FIG. 23 a sixth embodiment of a catheter end piece element in a perspective view, and FIG. 24 a sectional view of the catheter end piece element according to FIG. 23.

FIGS. 1 and 2 show a catheter 51 for aspiration, fragmentation and removal of removable material, in particular thrombi and emboli, from hollow bodies, in particular from blood vessels.

The catheter 51 comprises a flexible tube 52 having a proximal end 53 and a distal end 54.

Inside of the flexible tube 52 a flexible helical transport screw 62 is arranged, which extends from the proximal end 53 of the flexible tube in direction of the distal end of the flexible tube 52. The flexible helical transport screw 62 having a distal end 64. The flexible helical transport screw 62 is further provided with helically extending transport surfaces 65. The proximal end of the flexible helical transport screw 62 is connected to and is rotatable by a motor as a drive means 41.

A catheter end piece 72 is provided defining a part of a distal region 56 of the catheter 51. The catheter end piece 72 comprises a suction opening 74. The catheter end piece 72 is connected to the distal end 54 of the flexible tube 52.

A stopper element 82 for providing an abutment for the distal end 64 of the flexible helical transport screw 62 is provided spaced apart from the distal end of the catheter 51, thereby defining a distal region 56 of the catheter 51 extending from the stopper element 82 in direction to the distal end of the catheter 51. This distal region 56 of the catheter 51 is inside free of any rotational elements.

A guide wire 76 runs through the catheter 51 for guiding the catheter 51 inside of the vessel. The guide wire 76 may provide a support for the flexible helical transport screw 62 inside of the flexible tube 52.

For guiding of a catheter no guide wire is explicit needed. In an alternative embodiment the catheter is guided by other means, e.g., such as a pull wire to control the end piece direction.

In use, the catheter 51 is introduced, e.g., in a vessel for removing thrombi (blocking material) with its distal end ahead. The drive means 41 is actuated and thereby drives the flexible helical transport screw 62 from the proximal side. The rotating flexible helical transport screw 62 generates negative pressure which results in aspirating of the blocking material within the field of suction towards the suction opening 74. The negative pressure is produced by the high-speed rotation of the flexible helical transport screw 62 within the flexible tube 52. The blocking material is aspirated through the suction opening 74 provided in the distal region 56 of the catheter 51 into the inside of the catheter 51.

The aspirated material will then enter into the flexible tube 52 from the distal side of the stopper element 82. The aspirated material will enter through the stopper element 82. The transient changes in the flow pressure, while passing through the stopper element 82, as per venturi effects, causes an additional strain to the aspirated material and thus contributes to fragmenting the aspirated material.

Next, the aspirated material will be mechanically fragmented between the proximal edges or surface of the stopper element 82 and the distal end 64 of the rotating flexible helical transport screw 62.

The fragmented material will then be transported through the lumen of the flexible tube 52 outside the body by the rotating flexible helical transport screw 62.

FIGS. 3 and 4 show the stopper element 82 in more details. The stopper element 82 has a distal end 83 and a proximal end 88. The stopper element 82 has a sleeve-like shape with a first inner diameter D1 and a front opening 84 with a circumferential surface 85. The distal end 83 of the stopper element 82 comprises a rounded edge 86, which results in an advantageous flow behavior in this region.

The front opening 84 has a second inner diameter D2, whereby the second inner diameter D2 is smaller than the first inner diameter D1.

The stopper element 82 further comprises an abutment surface 87 for abutment of the distal end 64 of the flexible helical transport screw 62. The abutment surface 87 is provided inside of the stopper element 82.

The stopper element 82 may comprise at least partly radiopaque material.

FIGS. 5 and 6 show the stopper element 92. The stopper element 92 has also a sleeve-like shape. The front opening 94 has two circumferential surfaces 95 and 96. The first circumferential surface 95 is cylindrical shaped. The second circumferential surface 96 is conically shaped and is narrowing in the direction of the proximal end 98 of the stopper element 92. The embodiment of the front opening 94 influences advantageously the flow behavior in the lumen of the stopper element 92. The stopper element 92 also comprises an inside provided abutment surface 97 for abutment of the distal end of the flexible helical transport screw (not shown).

FIGS. 7 and 8 show the stopper element 102. The stopper element 102 has also a sleeve-like shape. The front opening 104 is provided with three circumferential surfaces 105, 106 and 109. The first circumferential surface 105 is cylindrical shaped. The second circumferential surface 106 is conically shaped and is narrowing in the direction of the proximal end 108 of the stopper element 102. The third circumferential surface 109 is also conically shaped and is also narrowing in the direction of the proximal end 108 of the stopper element 102. The length L1 of the second circumferential surface 106 in direction of the length axis 110 of the stopper element 102 is larger than the length L2 of the third circumferential surface 109 in direction of the length axis 110 of the stopper element 102. By choosing the respective lengths and/or the respective inner diameter of the circumferential surfaces 105, 106 or 109 the flow behavior in the lumen of the stopper element 102 can be influenced according the respective needs.

The stopper element 102 also comprises an inside provided abutment surface 107 for abutment of the distal end of the flexible helical transport screw (not shown).

FIGS. 9 and 10 show the stopper element 112, which compares from the embodiment mainly to the stopper element 92 as described in relation to FIGS. 5 and 6. However, inside of the stopper element 112 an additional abutment element 116 is arranged for providing an abutment for the distal end of the flexible helical transport screw (not shown). Advantageously, the additional abutment element 116 is made from a friction-low and/or abrasion-resistant material, e.g., as a non-exhaustive list from Teflon®, Polyamide or hard metals coated with low friction coatings.

FIG. 15 shows the stopper element 162 having a sleeve-like shape. The front opening 164 is provided with two bars 165 and 166, which intersect each other. Thereby, the front opening 164 is divided in four openings, each of equal size. At the intersection of the bars 165 and 166 a material reinforcement 167 is provided, which secures a sufficient stability, also if the bars 165 and 166 are of small size.

If a guide wire running inside of the stopper element 162 is provided, the material reinforcement 167 may be provided with a respective opening (not shown) for passing through the guide wire.

FIG. 11 shows a catheter 121 which compares to the catheter 51 according to FIGS. 1 and 2. In contrast to the catheter 51 a separate guide wire lumen 126 is provided at least party along to the flexible tube 122 of the catheter 121. Thereby a great lumen inside of the flexible tube 122 is provided for transporting the fragmented material outside the body. Thereby, a guidance of the catheter 121 inside the vessel is guaranteed.

FIGS. 12 and 13 show a catheter end piece 142, which is connected to a distal end on a flexible tube 132. On the proximal end 148 of the catheter end piece 142 an abutment surface 147 for abutment of the distal end of a flexible helical transport screw (not shown) is provided. The catheter end piece 142 defines the distal region of the catheter 131. The catheter end piece 142 comprising the two suction openings 144. The two suction openings 144 are arranged opposite of each other.

The catheter end piece 142 may comprise at least partly radiopaque material.

The catheter end piece 152 as shown by FIG. 14 compares in the embodiment mainly to the catheter end piece 142, as described in connection with FIGS. 12 and 13. However, a ring element 156 is provided which provides four suction openings 154 and 155, which are arranged opposite of each other, but two of them are different from size and form.

FIGS. 16 and 17 show the catheter end piece 172, which compares from the embodiment mainly to the catheter end piece 142 as described in relation to FIGS. 12 and 13. However, the catheter end piece 172 comprises apart from the two suction openings 174 a guide wire opening 176 for passing through a guide wire (not shown).

FIGS. 18 to 20 show the catheter end piece 192 which compares from the embodiment mainly to the catheter end piece 142 as described in relation to FIGS. 12 and 13. However, the catheter end piece 192 comprises apart from the two suction openings 194 a front suction opening 196 for providing a further opening to pass through a guide wire (not shown), whereby a respective area still is present for aspirating blocking material at the proximal end of the catheter.

Furthermore, the catheter end piece 192 comprises a connection section 198 in its proximal direction for connecting the catheter end piece 192 to the flexible tube 182. The catheter end piece 192 is further provided with a tube abutment surface 199 on which the distal end of the flexible tube 182 abuts, when the connection section 198 of the catheter end piece 192 is completely introduced in the flexible tube 182.

Inside of the catheter end piece 192 an abutment surface 197 for abutment of the distal end of a flexible helical transport screw 184 is provided.

FIGS. 21 to 22 show the catheter end piece 202 which has a sleeve-like shape and at the radial extending front section 212. Adjacent to the front section 212 extending to the proximal end of the catheter end piece 202 a connection section 218 is provided for connecting the catheter end piece 202 to a flexible tube of a catheter. The catheter end piece 202 is further provided with a tube abutment surface 214 on which the distal end of the flexible tube abuts when the connection section 218 of the catheter end piece 202 is completely introduced in the flexible tube. The front section 212 extends radially over the outer surface of the connection section 218.

The catheter end piece 202 comprises a front opening, whereby in the center of this front opening a guide wire sleeve 208 forming a guide wire opening 205 is arranged. The guide wire sleeve 208 is hold in position by two bars 206. Between the guide wire sleeve 208 and the inner circumferential surface of the front opening two suction openings 204 are provided.

Inside of the catheter end piece 202 an abutment surface 217 for abutment of the distal end of a flexible helical transport screw (not shown) is provided.

FIGS. 23 to 24 show the catheter end piece 222, which has a sleeve-like shape and at the distal end a collar section 232. Adjacent to the collar section 232 extending to the proximal end of the catheter end piece 222 a connection section 238 is provided for connecting the catheter end piece 222 to a flexible tube of a catheter. The catheter end piece 222 is further provided with a tube abutment surface 234 on which the distal end of the flexible tube abuts when the connection section 238 of the catheter end piece 222 is completely introduced in the flexible tube. The collar section 232 extends radially over the outer surface of the connection section 238.

The catheter end piece 222 comprises a front opening, whereby in the center of this front opening a guide wire sleeve 228 forming a guide wire opening 225 is arranged. The guide wire sleeve 228 is hold in position by one bar 226. Between the guide wire sleeve 228 and the inner circumferential surface of the front opening a suction opening 224 is provided.

Inside of the catheter end piece 222 an abutment surface 237 for abutment of the distal end of a flexible helical transport screw (not shown) is provided.

LIST OF REFERENCE SIGNS 41 drive means (motor)
51 catheter
52 flexible tube
53 proximal end of 52
54 distal end of 52
56 distal region of 51
62 flexible helical transport screw
64 distal end of 62
65 transport surfaces of 62
72 catheter end piece
74 suction opening
76 guide wire
82 stopper element
83 distal end of 82
84 front opening
85 circumferential surface
86 edge
87 abutment surface
88 proximal end of 82
D1 $1^{st}$ inner diameter
D2 $2^{nd}$ inner diameter
92 stopper element
94 front opening
95 $1^{st}$ circumferential surface
96 $2^{nd}$ circumferential surface
97 abutment surface
98 proximal end of 92
102 stopper element
104 front opening
105 $1^{st}$ circumferential surface
106 $2^{nd}$ circumferential surface
107 abutment surface
108 proximal end of 102
109 $3^{rd}$ circumferential surface
110 length axis
112 stopper element
116 additional abutment element
117 abutment surface
121 catheter
122 flexible tube
126 guide wire lumen
131 catheter
132 flexible tube
142 catheter end piece
144 suction opening
147 abutment surface
148 proximal end of 142
152 catheter end piece
154 suction opening
155 suction opening
156 ring element
162 stopper element
164 front opening
165 bar
166 bar
167 material reinforcement
172 catheter end piece
174 suction opening
176 guide wire opening
182 flexible tube
184 flexible helical transport screw
192 catheter end piece
194 suction opening
196 guide wire opening
197 abutment surface
198 connection section of 192
199 tube abutment surface
202 catheter end piece
204 suction opening
205 guide wire opening
206 bar
208 guide wire sleeve
212 front section
214 tube abutment surface
217 abutment surface
218 connection section of 202
222 catheter end piece
224 suction opening
225 guide wire opening
226 bar
228 guide wire sleeve 232 collar section
234 tube abutment surface
237 abutment surface
238 connection section of 202

The invention claimed is:

1. Catheter for aspiration, fragmentation and removal of removable material, in particular thrombi and emboli, from hollow bodies, in particular blood vessels, comprising:
a flexible tube, the flexible tube having a proximal end and a distal end,
a flexible helical transport screw, the flexible helical transport screw extending from the proximal end of the flexible tube inside of the flexible tube in direction of the distal end of the flexible tube and the flexible helical transport screw having a distal end, wherein said flexible helical transport screw is provided with helically extending transport surfaces and is rotatable by a drive means,
a stopper element located inside the flexible tube and engaging an inner surface of the flexible tube, the stopper element configured to provide an abutment for the distal end of the flexible helical transport screw as the distal end of the flexible helical transport screw travels distally relative to the stopper element, wherein the stopper element is provided spaced apart from the distal end of the catheter, thereby defining a distal region of the catheter extending from the stopper element in direction to the distal end of the catheter, which is free of rotational elements inside,
at least one suction opening for aspiration of said removable material into the inside of the flexible tube, wherein the at least one suction opening is provided in the distal region of the catheter.

2. Catheter according to claim 1, wherein the stopper element having a distal end and a proximal end and the stopper element having a sleeve-like shape with a first inner diameter and a distal front opening having at least one circumferential surface and at least partly at least one abutment surface for abutment for the distal end of the flexible helical transport screw.

3. Catheter according to claim 1, wherein the stopper element having a distal end and a proximal end and the stopper element having a sleeve-like shape with a first inner diameter and a distal front opening having at least a second inner diameter and at least one circumferential surface, whereby the at least second inner diameter is smaller than the first inner diameter.

4. Catheter according to claim 2, wherein the at least one circumferential surface of the distal front distal opening of the stopper element is conically shaped, in particular narrowing in the direction of the proximal end of the stopper element.

5. Catheter according to claim 1, wherein the stopper element comprising an additional abutment element for providing an abutment of the distal end of the flexible helical transport screw, wherein in particular the additional abutment element is provided inside of the stopper element.

6. Catheter according to claim 1, wherein the stopper element comprises at least partly radiopaque material.

7. Catheter according to claim 1, wherein a catheter end piece is provided, defining at least partly the distal region of the catheter, wherein the catheter end piece comprising the at least one suction opening and wherein catheter end piece is connected to the distal end of the flexible tube.

8. Catheter according to claim 7, wherein the catheter end piece comprising at least two suction openings, which at least two suction openings are in particular arranged opposite of each other.

9. Catheter according to claim 7, wherein the catheter end piece comprising at least one suction opening at the distal end of the catheter end piece.

10. Catheter according to claim 7, wherein the stopper element is an abutment surface provided inside of the catheter end piece.

11. Catheter according to claim 7, wherein the catheter end piece comprising a guide wire opening for pass through the guide wire through the catheter end piece.

12. Catheter according to claim 11, wherein the guide wire opening of the catheter end piece is arranged at least partly inside of the at least one suction opening.

13. Catheter according to claim 7, wherein the catheter end piece comprising a connection section for connecting the catheter end piece to the flexible tube.

14. Catheter according to claim 7, wherein the catheter end piece comprises at least partly radiopaque material.

* * * * *